(12) United States Patent
Dandala et al.

(10) Patent No.: US 7,105,659 B2
(45) Date of Patent: Sep. 12, 2006

(54) PROCESS FOR PREPARING CEFDINIR

(75) Inventors: Ramesh Dandala, Hyderabad (IN); V. V. Prasada Rao Korrapati, Hyderabad (IN); Meenakhshisunderam Sivakumaran, Hyderabad (IN)

(73) Assignee: Aurobind - Pharma Ltd., Hyderabad (IN)

( * ) Notice: Subject to any disclaimer, the term of this patent is extended or adjusted under 35 U.S.C. 154(b) by 289 days.

(21) Appl. No.: 10/676,914

(22) Filed: Oct. 1, 2003

(65) Prior Publication Data

US 2004/0242557 A1 Dec. 2, 2004

(30) Foreign Application Priority Data

Jun. 2, 2003 (IN) .................. 441/MAS/2003

(51) Int. Cl.
*C07D 501/22* (2006.01)
(52) U.S. Cl. .................................... 540/222
(58) Field of Classification Search ........ 540/222
See application file for complete search history.

(56) References Cited

U.S. PATENT DOCUMENTS

| 4,888,429 | A | * | 12/1989 | Hebeisen | 548/194 |
|---|---|---|---|---|---|
| 5,523,400 | A | * | 6/1996 | Wei et al. | 514/202 |
| 6,878,827 | B1 | * | 4/2005 | Ono et al. | 548/194 |
| 2003/0204082 | A1 | * | 10/2003 | Manca et al. | 540/222 |
| 2004/0210049 | A1 | * | 10/2004 | Lee et al. | 540/222 |
| 2004/0242556 | A1 | * | 12/2004 | Dandala et al. | 514/202 |
| 2005/0080255 | A1 | * | 4/2005 | Kumar et al. | 540/222 |
| 2005/0137182 | A1 | * | 6/2005 | Dandala et al. | 514/202 |
| 2006/0025586 | A1 | * | 2/2006 | Kremminger et al. | 540/222 |

FOREIGN PATENT DOCUMENTS

| JP | 59-184186 | * | 10/1984 |
|---|---|---|---|
| JP | 02000790 A2 | * | 1/1990 |
| WO | WO 0179211 A1 | * | 1/2001 |
| WO | WO 2004016623 A1 | * | 2/2004 |

OTHER PUBLICATIONS

Translation of WO0179211 A1.*
Lin, Hecheng Huaxue 9(5) 383-385 2001 and translation.*
Translation of JP 02000790 A2.*

* cited by examiner

*Primary Examiner*—Mark L. Berch
(74) *Attorney, Agent, or Firm*—Jay R Akhave

(57) ABSTRACT

The present invention relates to a novel process for the preparation of a cefdinir

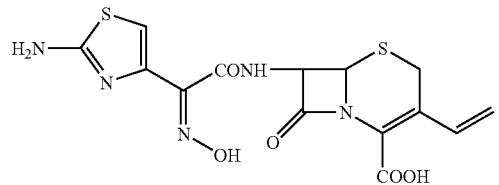

by reacting O-acetyl thioester of Formula I Formula I

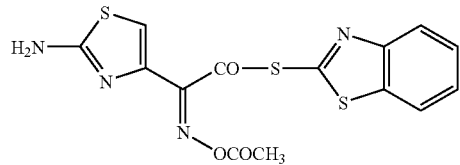

with

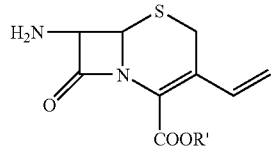

in the presence of a base in suitable solvent wherein R' represents H or any carboxyl protecting group, and then converting to the cefdinir by the removal of protecting groups. This invention also relates to making the cefdinir using a novel process to prepare the O-acetyl thioester intermediate (Formula I) by condensing (Z)-2-(2-amino-4-thiazolyl)-2-acetyloxyiminoacetic acid with bis(benzothiazol-2-yl)disulphide in the presence of triphenylphosphine and a base in a suitable solvent.

10 Claims, No Drawings

PROCESS FOR PREPARING CEFDINIR

BACKGROUND OF THE INVENTION

Cefdinir of Formula II is an oral, semi-synthetic cephalosporin antibiotic characterized by having a broad spectrum of antibacterial activity particularly against *Staphylococci* and *Streptococci* and a high stability against various β-lactamases. It further exhibits an enhanced activity against gram-positive bacteria as well and is chemically known as 7β-[(Z)-2-(2-amino-4-thiazolyl)-2-hydroxyiminoacetamido]-3-vinyl3-cephem-4-carboxylic acid.

Several synthetic methods are known in literature for preparation of cefdinir. For example, U.S. Pat. No. 4,559,334 describes a synthetic method starting from benzhydryl 7-amino-3-vinyl-3-cephem-4-carboxylate which is reacted with 4-bromoacetoacetyl bromide, the resulting product is nitrosated to oxime and cyclized to obtain protected cefdinir. Deprotection yielded cefdinir (Refer Scheme-1). However, this synthetic method suffers from several disadvantages such as use of not so easily available raw materials, low yielding steps and isolation involving chromatography and lyophilisation. Overall yield reported is 10–11%.

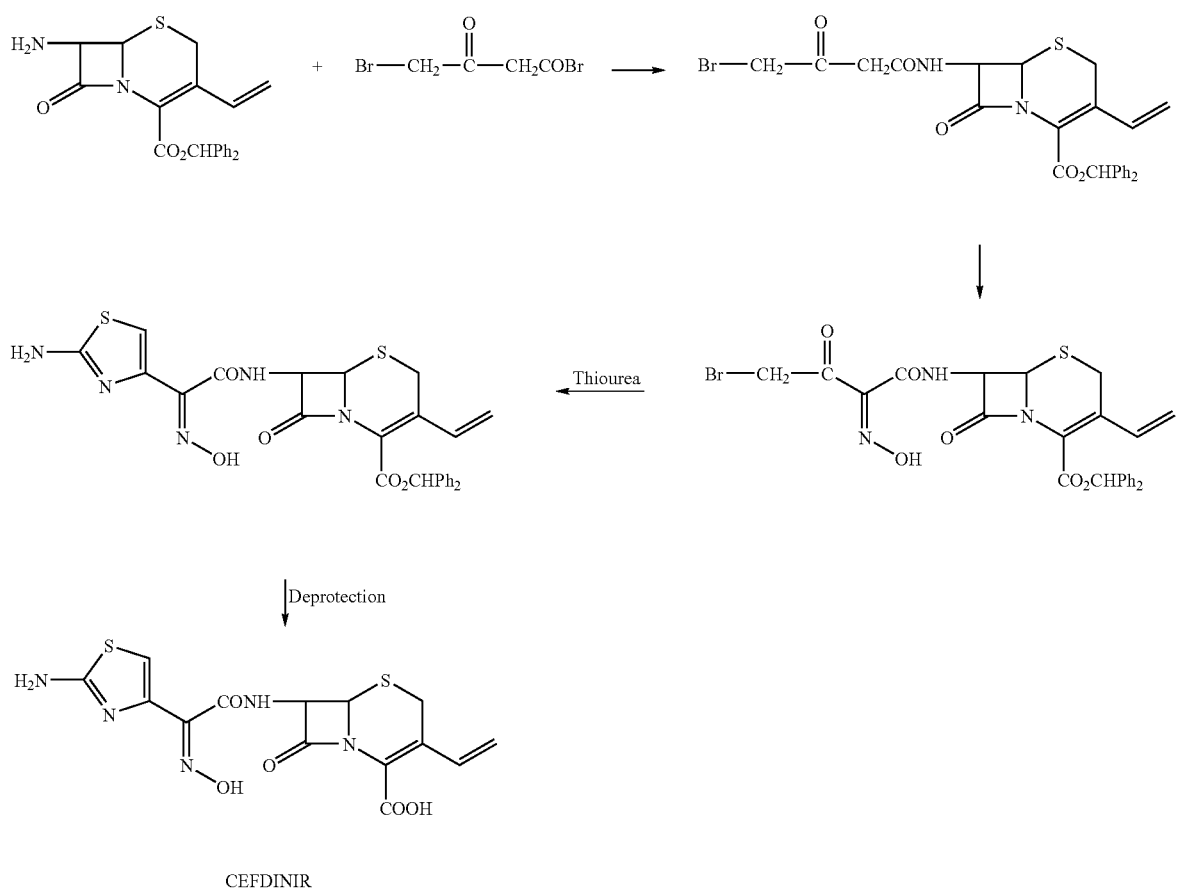

Ph: Phenyl

Spanish Patent ES 2 013 828 describes alternate route to prepare Cefdinir overcoming the difficulties in U.S. Pat. No. 4,559,334 (Refer Scheme-2).

Thus, (Z)-2-(2-amino-4-thiazolyl)-2-acetyloxyiminoacetic acid was prepared and converted into corresponding acid chloride hydrochloride (A) via reaction with phosphorus pentachloride and condensed with 7-amino-3-vinyl-3-cephem-4-carboxylic acid to yield O-acetyl Cefdinir which was deprotected to yield Cefdinir.

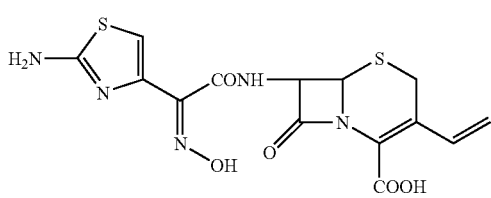

Formula II

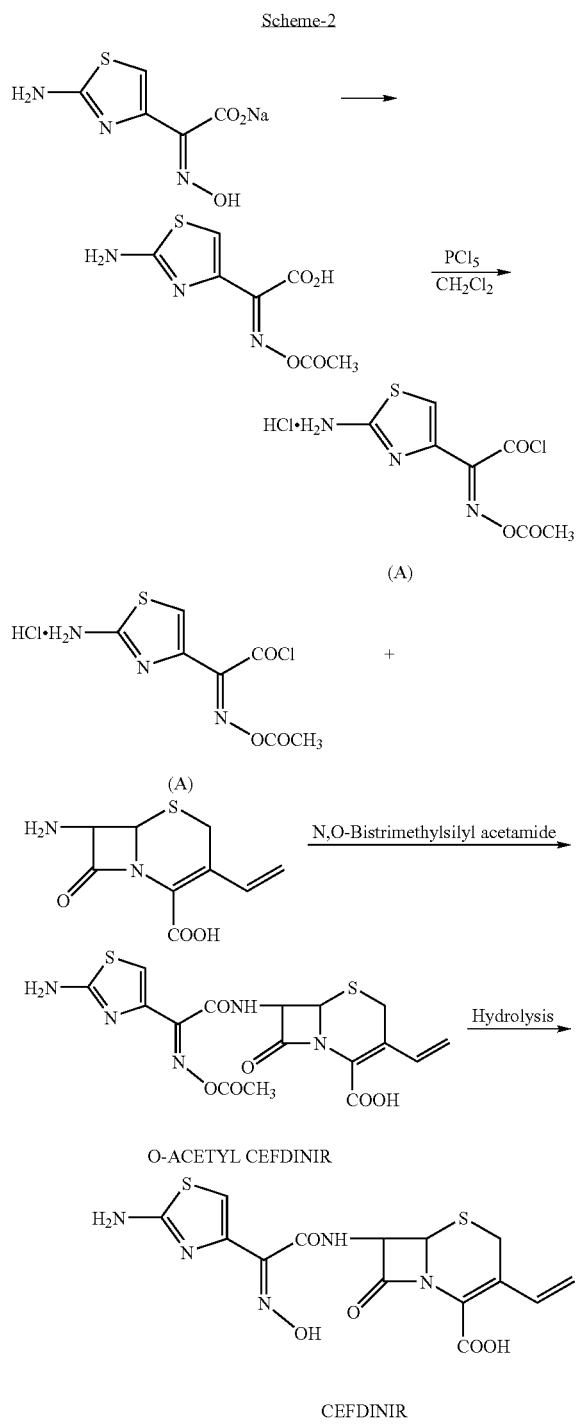

Scheme-2

(A)

O-ACETYL CEFDINIR

CEFDINIR

However, in our hands the preparation of (Z)-2-(2-amino-4-thiazolyl)-2-acteyloxyiminoacetylchloride hydrochloride did not prove to be consistent, possibly due to nature of side chain sodium salt and a lot of impurity formation was observed. Moreover this reaction resulted in incomplete conversion and formation of anti-isomer was also observed. Further, this process requires very low temperature leading to additional burden on equipment.

U.S. Pat. No. 6,093,814 describes a process wherein tritylated cefdinir is prepared and isolated as O-trityl cefdinir.p-toluenesulfonic acid.2N,N-dimethylacetamide solvate and further converted into cefdinir either by treatment with formic acid or trifluoroacetic acid (Refer Scheme-3). The disadvantages of this process are use of ethers to isolate O-trityl cefdinir.p-toluenesulfonic acid.2N,N-dimethylacetamide solvate which greatly enhances danger of fire hazard on a commercial scale and poor solvent recovery. Further, we could not realize the specified yields in detritylation step.

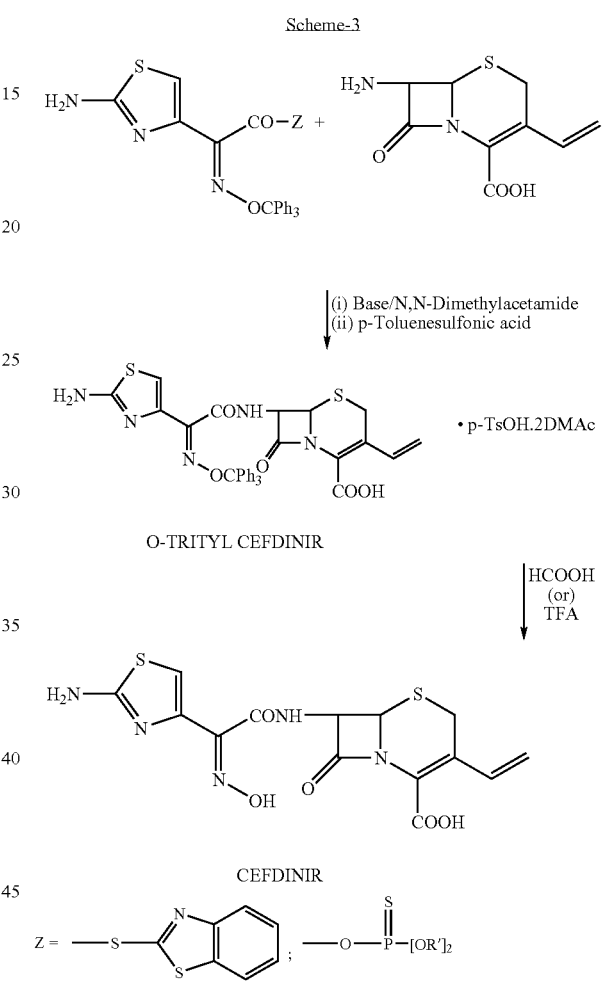

Scheme-3

O-TRITYL CEFDINIR

CEFDINIR

Ph = Phenyl

Detritylation to obtain cefdinir by using a perhalogenated acids has been described by Otsuka Chemical Company in EP 1 273 587 A1. However, this process also gave low yields and further handling and disposal of perhalogenated acids poses an industrial hazard.

Thus, it is evident that the intermediates described in the prior art to prepare Cefdinir include an acid chloride, a reactive thiophosphate, a reactive ester and the like. However, these intermediates have some disadvantages such as low yields, expensive input raw materials and handling problem in commercial production. Hence, there is a need to use such acylating agent which is capable of transferring the 2-aminothiazolyl moiety to 7-amino-3-cephem compound in good yield without producing any side product and without requiring complicated protection/deprotection operations.

DETAILED DESCRIPTION OF THE INVENTION

The instant invention relates to an industrially advantageous process for the preparation of cefdinir, which involves the use of intermediate, 2-mercaptobenzothiazolyl (Z)-2-(2-amino-4-thiazolyl)-2-acetyloxyiminoacetate (O-acetyl thioester), of Formula I

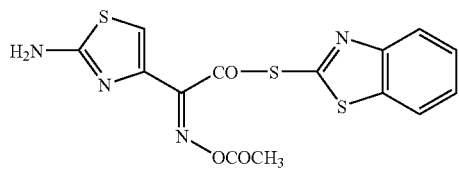

Formula I

2-Mercaptobenzothiazolyl (Z)-2-(2-amino-4-thiazolyl)-2-acetyloxyiminoacetate (O-acetyl thioester), of Formula I was reported in U.S. Pat. No. 4,888,429, but its use to prepare Cefdinir has never been reported and constitutes novelty.

Further, the present invention provides a new method for the preparation of intermediate, O-acetyl thioester and its valuable use in the preparation of pure cefdinir.

The intermediate, O-acetyl thioester can be prepared by condensation of (Z)-2-(2-amino-4thiazolyl)-2-aceyloximinoacetic acid with bis(benzothiazol-2-yl)disulphide, in the presence of triphenylphosphine and a base in a suitable solvent at 0–35° C. (Refer Scheme-4).

(Z)-2-(2-amino-4-thiazolyl)-2-acetyloxyiminoacetic acid for the preparation of O-acetyl thioester is prepared by known process as described in ES 2 013 828. The commercially available ethyl (Z)-2-(2-amino-4-thiazolyl)-2-hydroxyiminoacetate is treated with aqueous sodium hydroxide in ethanol to yield corresponding sodium salt. The resulting sodium salt is acylated with acetic anhydride maintaining pH between 7.0 to 8.0 using potassium carbonate to yield (Z)-2-(2-amino-4-thiazolyl)-2-acetyloxyiminoacetic acid (acylated acid). We have observed that variation in pH results in the formation of diacylated product. The acylated acid typically has ~14% of moisture content. It is preferable to use dehydrated acylated acid for the preparation of O-acetylthioester. Use of dehydrated acylated acid avoids the excess consumption of reagents and minimizes exothermicity. Dehydration can be carried out in any suitable solvent like methanol, ethanol, acetone etc., but most preferably dehydration is effected in acetone to obtain acylated acid having moisture content ≦0.5%. This dehydrated acylated acid can preferably be used in preparation of O-acetyl thioester as discussed above.

Thereafter, the O-acetyl thioester of Formula I is reacted with cephem of Formula III in the presence of a base, in any suitable solvent at a temperature range of 10–25° C. but preferably at 20–25° C.

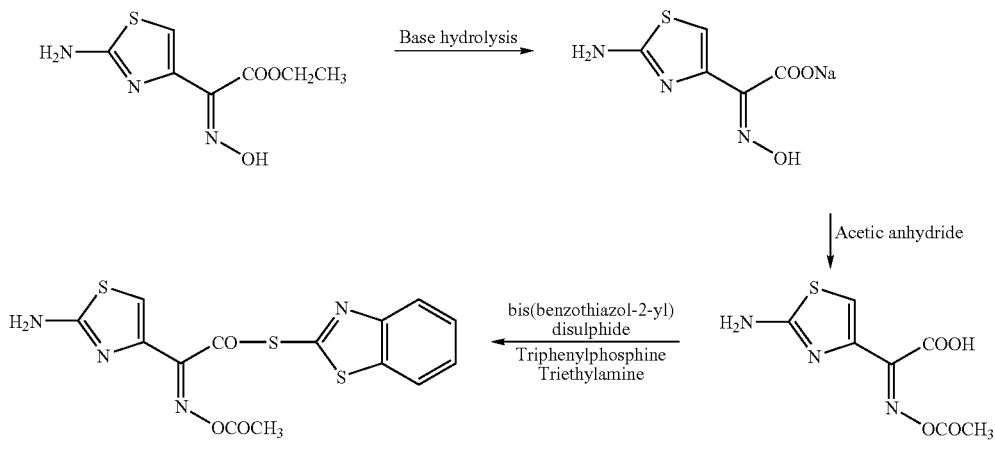

Scheme-4

Formula I

Suitable solvents can be selected from a group of methylene dichloride, chloroform tetrahydrofuran, acetonitrile or like and mixture thereof; but the most preferred ones are methylene dichloride and tetrahydrofuran.

Typically reaction can be conducted at a temperature range of about 0–35° C., but preferably at, 10–30° C. The bases, which can be used, are tertiary organic bases such as tributylamine, triethylamine or like, but preferably triethylamine is used. After completion of reaction, the product which precipitates out spontaneously from the reaction mass is isolated by filtration.

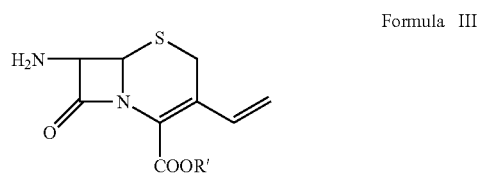

Formula III

R' in compound of Formula III may be any carboxyl protecting group. The term carboxyl protecting group as used herein refers to a protecting group which is conventionally used in cephalosporin based compounds and exemplary protecting group includes silyl group; alkyl esters such as methyl and t-butyl; alkoxylkyl such as methoxymethyl; alkyl thioalkyl esters such as methyl, thiomethyl; haloalkyl esters such as 2,2,2-trichloroethyl and aralkyl ester, such as benzyl, p-methoxybenzyl, p-nitrobenzyl, diphenylmethyl; wherein p-methoxybenzyl, p-nitrobenzyl and diphenylmethyl are preferred.

The suitable solvent can be selected from a group of water, tetrahydrofuran, methylene dichloride or mixture thereof, but preferably solvent is aqueous tetrahydrofuran.

The base can be selected from inorganic bases such as sodium bicarbonate, sodium carbonate or organic bases such as alkylamines preferably tertiary alkylamines like triethylamine, diisopropylethylamine, tributylamine etc. Particularly preferred base is triethylamine.

The progress of reaction is monitored by HPLC till cephem of Formula III (R'=H) is less than 1%. Thereafter reaction mass is diluted with any suitable solvent and O-acetyl cefdinir is extracted with water. O-Acetyl cefdinir is optionally isolated and can also be deprotected in situ to obtain Cefdinir.

The major advantages realized in the present inventions are preparation of O-acetyl thioester which offers the best feature of acylation to introduce side chain on compound of Formula III and preparation of O-acetyl cefdinir in good yields and high purity. Such a methodology overcomes the difficulties experienced in the prior art such as low yields, poor quality and handling problem in commercial production.

Hence the present invention for the preparation of cefdinir is suitable for plant scale production and Cefdinir is obtained in high yield and high quality consistently.

Further the following examples will illustrate the preparation of O-acetyl thioester and cefdinir per this invention and these examples should not to be construed to be limiting the invention in any way.

EXAMPLE 1

PREPARATION OF 2-MERCAPTOBENZOTHIAZOLYL (Z)-2-(2-AMINO-4-THIAZOLYL)-2-ACETYLOXYIMINOACETATE (O-ACETYL THIOESTER)

55 g of (Z)-2-(2-amino-4-thiazolyl)-2-acetyloxyiminoacetic acid (0.240 mol, moisture content: 0.49% w/w) was added to 825 ml of methylene dichloride at 20° C. Cooled the reaction mass to 15–20° C. To this mixture, 111.6 g of bis(benzothiazol-2-yl)disulphide (0.336 mol) and 91.2 g of triphenylphospine (0.348 mol) were added at 10–15° C. To this reaction mixture, 34 g of triethylamine (0.336 mol) was added at 10–15° C. during a period of 5–10 min. Maintained the reaction mass temperature at 10–30° C. till starting material is ≦2% by qualitative HPLC analysis (~1 h). Cooled the reaction mixture to 5–10° C. and filtered the precipitated product. Washed with 300 ml of methylene dichloride at 5–10° C. Dried the product at 35–40° C. under reduced pressure till LOD≦1% w/w. 74 g of product was isolated which showed greater than 94% purity by HPLC with a melting point of 143–145° C.

| INFRARED ABSORPTION: SPECTRUM (IR) ($Cm^{-1}$, KBr) | 3446, 3101, 1777, 1645, 1618 |
|---|---|
| $^1$H-NMR in DMSO-$d_6$: | δ(ppm); 2.23 (s, 3 H); 7.38(s, 1 H); 7.52 (.2H); 7.55–7.65 (m, 2 H); 8.09 (d, 1 H, J = 9 Hz), 6.23 (d, 1 H, J = 9 Hz). |

EXAMPLE 2

PREPARATION OF 7β-[(Z)-2-(2-AMINO-4-THIAZOLYL)-2-HYDROXYIMINO ACETAMIDO]-3-VINYL-3-CEPHEM-4-CARBOXYLIC ACID (CEFDINIR)

40 g of 7-amino-3-vinyl-3-cephem-4-carboxylic acid (AVNA, 0.177 mol) was added to 400 ml of tetrahydrofuran under nitrogen atmosphere followed by 78 g of O-acetyl thioester (0.206 mol, prepared in Example 1) and 200 ml of water with stirring. Cooled the reaction mass to 15–20° C. To this reaction mixture, 20 g of triethylamine was added slowly at pH ~8.5. Stirring was continued and progress of the reaction was monitored by qualitative HPLC till AVNA was less than 1%. At this stage 400 ml of methylene dichloride was added and stirred for further 15 min at 20–25° C. 200 ml of water was added and stirred the reaction mass for 15 min at 20–25° C. Separated the layers and to the aqueous layer, 20% w/v aqueous potassium carbonate solution was added and maintained pH at 8.1–8.2 at 20–25° C. Thereafter, 26.4 g of ammonium chloride was added in one lot at 20–25° C. and continued maintaining the pH between 8.0 to 8.2 by addition of 20% w/v aqueous potassium carbonate solution. The progress of reaction was monitored by qualitative HPLC till O-acetyl cefdinir is less than 0.5%. Adjusted the pH of reaction mass to 2.4–2.5 with conc. sulfuric acid maintaining temperature between 35° to 40° C. The precipitated product was filtered and dried at 40–45° C. under reduced pressure till moisture content was ≦2% w/w. 44 g of product was obtained in 99.3% purity (by HPLC).

What is claimed is:

1. A process for preparing a cefdinir of Formula II

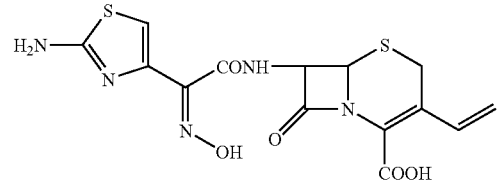

Formula II comprising the steps of:
reacting O-acetyl thioester of Formula I

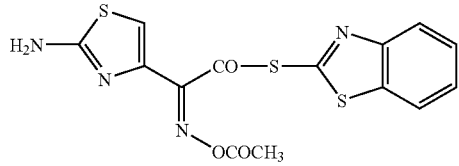

Formula I with a compound of Formula III in the presence of a base in suitable solvent

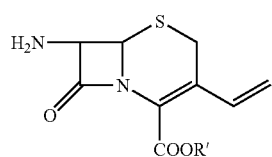

Formula III wherein R' represents H or any carboxyl protecting group or a silyl group, converting to cefdinir by the removal of protecting group or groups.

2. The process according to claim 1 wherein the said base is an organic base selected from the group consisting of triethylamine, N,N-diisopropylethylamine, tributylamine.

3. The process according to claim 1 wherein the said base is an inorganic base selected from the group consisting of sodium carbonate, sodium bicarbonate and mixtures thereof.

4. The process according to claim 1 wherein the said solvent is selected from the group consisting of water, tetrahydrofuran, methylene dichloride and mixtures thereof.

5. The process according to claim 1 wherein the said reacting step is conducted at a temperature between 10° C. and 25° C.

6. The process according to claim 1 wherein the said carboxyl protecting group is selected from the group consisting of p-methoxybenzyl, p-nitrobenzyl, or diphenylmethyl.

7. The process according to claim 1 wherein the said O-acetyl thioester of Formula I

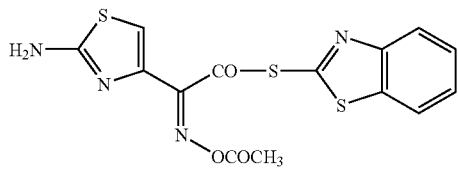

Formula I is prepared by a process which comprises of
condensing (Z)-2-(2-amino-4-thiazolyl)-2-acetyloxyiminoacetic acid with bis(benzothiazol-2-yl)disulphide in the presence of triphenylphosphine and a base in a suitable solvent.

8. The process according to claim 7 wherein the base used in the preparation of compound of Formula I is selected from the group consisting of tributylamine, triethylamine and mixtures thereof.

9. The process according to claim 7 wherein the said solvent used in the preparation of compound of Formula I is selected from the group consisting of methylene chloride, chloroform, tetrahydrofuran, acetonitrile and mixtures thereof.

10. The process according to claim 7 wherein the said condensing step in the preparation of compound of Formula I is conducted at a temperature between 0° C. and 35° C.

* * * * *